United States Patent [19]

Greene et al.

[11] Patent Number: 5,464,751
[45] Date of Patent: Nov. 7, 1995

[54] LIGAND FOR THE NEU GENE PRODUCT

[75] Inventors: Mark I. Greene, Penn Valley, Pa.; Kunio Dobashi, Gunma, Japan; James G. Davis, Philadelphia, Pa.; Junji Hamuro, Yokahama, Japan

[73] Assignee: Trustees of the University of Pennsylvania, Philadelphia, Pa.

[21] Appl. No.: 927,422

[22] PCT Filed: Apr. 4, 1991

[86] PCT No.: PCT/US91/02331

§ 371 Date: Sep. 24, 1992

§ 102(e) Date: Sep. 24, 1992

[87] PCT Pub. No.: WO91/15230

PCT Pub. Date: Oct. 17, 1991

Related U.S. Application Data

[63] Continuation-in-part of Ser. No. 505,837, Apr. 6, 1990, abandoned.

[51] Int. Cl.$^6$ ................................................. G01N 33/574
[52] U.S. Cl. .................... 435/7.23; 436/64; 436/813; 530/350; 530/395; 530/397; 530/399; 530/828
[58] Field of Search .......................... 435/7.23; 436/64, 436/813; 530/350, 399, 397, 828, 395

OTHER PUBLICATIONS

Lupu, R., et al., *Princess Takamatsu Symp.*, vol. 22, pp. 49–60, 1991 (Abstract Only).

Matrisian, et al., "Further Purification of Epidermal Growth Factor by High Performance Liquid Chromatography," *Anal. Biochem.* 125(2), pp. 339–351, 1982. Abstract only.

Drebin et al., "Down–Modulation of an Oncogene Protein Product and Reversion of the Transformed Phenotype by Monoclonal Antibodies," *Cell* 41:695–706, 1985.

Drebin et al., "Monoclonal antibodies reactive with distinct domains of the neu oncogene–encoded p185 molecule synergistic anti–tumor effects in vivo," *Oncogene* 2:273–277, 1988.

Yarden et al., "Experimental approaches to hypothetical hormones: Detection of a candidate ligand of the neu protooncogene," *Proc. Natl. Acad. Sci. USA* 86:3179–3183, 1989.

Williams et al., "Platelet–derived Growth Factor Receptors Form a High Affinity State in Membrane Preparations," *J. Biol. Chem.* 259:5287–5294, 1984.

Weiner et al., "A point mutation in the neu oncogene mimics ligand induction of receptor aggregation," *Nature* 339:230234, 1989.

Wada et al, "Intermolecular Association of the p185$^{neu}$ Protein and EGF Receptor Modulates ECF Receptor Function," *Cell* 61:1339–1347, 1990.

Di Fiore et al., "Overexpression of the Human EGF Receptor Confers on EGF-Dependent Transformed Phenotype to NIH 3T3 Cells," *Cell* 51;1063–1070, 1987.

Kokai et al., "Phosphorylation Process Induced by Epidermal Growth Factor Alters the Oncogenic and Cellular Neu NGL Gene Products," *Biological Abstracts* BA86:91443, 1988.

Stern et al., "EGF–Stimulated Tyrosine Phosphorylation of P185N–E–U A Potential Model for Receptor Interactions," *Biological Abstracts* BA87:44442, 1988.

Yarden et al., "Epidermal Growth Factor Induces Rapid, Reversible Aggregation of the Purified Epidermal Growth Factor Receptor," *Biochem.* 26:1443–1451, 1987.

Kokai et al., "Synergistic Interaction of p185c–neu and the EGT Receptor Leads to Transformation of Rodent Fibroblasts," *Cell* 58:287–292, 1989.

Bishayee et al, "Ligand–induced Dimerization of the Platelet–derived Growth Factor Receptor," *J. of Biol. Chem.* 264:11699–11705, 1989.

Drebin et al., "Monoclonal antibodies identify a cell–surface antigen associated with an activated cellular oncogene," *Nature* 312:545–548, 1984.

Yarden et al, "Growth Factor Receptor Tyrosine Kinases," *Ann. Rev. Biochem.* 57:443–78, 1988.

Maguire et al., "Distribution of neu (c–erbB–2) Protein in Human Skin," *Investigative Dermatology* 92:786–790, 1989.

Cohen et al., "Expression pattern of the neu (NGL) gene–encoded growth factor receptor protein (p185$^{neu}$) in normal and transformed epithelial tissues of the digestive tract," *Oncogene* 4:81–88, 1989.

Kokai et al., "Stage– and tissue–specific expression of the neu oncogene in rat development," *Proc. Natl. Acad. Sci. USA* 84:8498–8501, 1987.

Greene et al., "Receptor Systems in Tissues of the Nervous System," *Immunological Reviews* No. 100. Dec. 1987.

*Primary Examiner*—Toni R. Scheiner
*Attorney, Agent, or Firm*—Woodcock Washburn Kurtz Mackiewicz & Norris

[57] ABSTRACT

A purified proteinaceous substance bindable with p185, the translation product of the neu oncogene is disclosed. The purified proteinaceous substance may be characterized in that it increases the activity of the tyrosine kinase contained in the neu oncogene product but does not increase the activity of tyrosine kinase of epidermal growth factor receptor; induces p185 dimerization and internalization; affects the growth of cells which express p185 in a dose dependent manner; is heat stable from about 56° C. to about 100° C.; is degradable by protease; and has a molecular weight of from about 7,000 to about 14,000 daltons in its smallest active form as determined by gel filtration and ultrafiltration membrane analysis. Methods of detecting p185 on the surfaces of tumor cells are also disclosed.

14 Claims, No Drawings

LIGAND FOR THE NEU GENE PRODUCT

REFERENCE TO RELATED APPLICATION

This application is a continuation-in-part of U.S. Ser. No. 505,837 filed on Apr. 6, 1990, now abandoned, which is assigned to the assignee of this application and is incorporated by reference herein.

FIELD OF THE INVENTION

The present invention relates to the field of substances useful for modulating the metabolism of cells; more particularly the present invention relates to the field of proteinaceous substances useful for modulating the metabolism of cells.

BACKGROUND OF THE INVENTION

The neu gene product is a transmembrane growth-factor-receptor-like tyrosine kinase. It was originally isolated from chemically induced rat neuroblastomas that developed in the offspring of rodents exposed to ethylnitrosourea at a discrete time period of gestation. The chemically induced mutagenic event results in a point mutation (an adenine to thymidine) in the neu gene at the nucleotide level which translates into a single amino acid substitution (valine to glutamic acid) in the neu gene product's transmembrane region. The tyrosine kinase domain of the rat neu gene product becomes constitutively activated by this point mutation in its transmembrane region. The neu gene encodes a 185 Kd surface glycoprotein, termed p185, that possesses tyrosine kinase activity and is structurally similar to the epidermal growth factor receptor (EGFR) at the nucleotide and amino acid level. However, the neu gene has been shown to be distinct from the epidermal growth factor receptor-encoding gene (the c-erb-B gene) by detailed molecular analysis and chromosomal localization studies. The neu gene product's similarity with the epidermal growth factor receptor (EGFR) suggests that p185 is also a growth factor receptor of an as yet unidentified growth modulating factor. The rat and human neu genes are 90% homologous. The relative molecular masses of their protein products differ slightly, Mr=185 kDa for the rat protein and 190 kDa for the human protein. This discrepancy is thought to result from interspecies differences in post-translational modification. See Greene, M. I. et al., "Receptor Systems in Tissues of the Nervous System", *Immunological Reviews*, Number 100, December 1987 for a review of the neu oncogene, its product and function.

The neu gene and neu gene product refers herein to all mammalian and vertebrate homologies of this gene and its protein product. As used herein, the oncogenic form of the rat neu gene product will be denoted as p185neu. The normal cellular non-oncogenic gene product will be denoted as p185c-neu. The human homologue of the rat neu gene product is referred to herein as c-erb-B-2 or human neu. p185 written alone broadly refers herein to rat and human and other mammalian homologues of the rat neu gene product. p185 involvement in neoplasia and its growth factor receptor like attributes suggest that p185 protein plays an important role in normal and abnormal growth and differentiation of the cells in which it is expressed.

p185 has been found in variety of tissues derived from developing and adult animals in a developmental stage and tissue specific manner, Kokai, Y. et al., (1987) *Proc. Natl. Acad. Sci. U.S.A.* 84: 8498–8501; Maguire, H. C. et al., (1989) *J. Investigative Dermatology* 92: 786–790; Cohen, J. A. et al, (1989) *Oncogene* 4: 81–88. Expression of p185 in the adult rat and human has been detected in the epithelial layers of intestinal villi, basal layer and hair follicles of the skin, pulmonary bronchioles, proximal renal tubules, fallopian tubes, mammary ducts, bladder, and uterine endometrium and in some developing and adult peripheral and central glial cells. Neural and connective tissues express neu during a relatively narrow time window in mid to late gestation, but show no expression in the adult. In secretory epithelial layers of other organs, expression of the neu gene persists into adulthood. Lymphoid tissues do not appear to express the neu gene at any developmental stage.

p185c-neu is expressed on the surface of a number of normal cell types and on the surface of some tumors. Minimal expression of p185c-neu has been found in ependyma, choroid plexus, ciliary body, terminal bronchial epithelium, ovarian stromal epithelium and the loop of Henle. Genitourinary epithelium and normal skin appendages had slightly higher expression. These tissues include bladder transitional epithelium, fallopian tube epithelium, bile duct, collecting duct, endometrial gland epithelium, epidermis, hair follicles, sebaceous gland, and uretheral epithelium. Higher expression of p185 has been found in the rapidly dividing tissues of breast and gastrointestinal tissue. These structures include breast alveolar and ductal epithelium, hepatocytes, proximal and distal tubules, pancreatic islet cells, and gastric mucosa. The highest levels of p185 expression have been found in the rapidly dividing tissues of secretory epithelium and include the meibomian gland of the eye, the cornea, intestinal villus epithelium, pancreatic acinus, pancreatic ductal epithelium, and salivary ductal epithelium. Differential expression of p185 has been found in several types of tissues. In the kidney, the proximal and distal tubules have high expression, whereas there is diminished expression in the Loop of Henle. In the small bowel epithelium, there is minimal expression in the crypts, with gradually increasing expression as the villus tip is reached. In skin, there is minimal expression in the basal layers and increasing expression in the epidermis. There is also staining in the hair follicles.

In human and rat tissues, static tissues and tissues with a slow rate of adult cellular turnover do not express p185. These tissues are of endodermal and mesodermal origin and included lymphoid tissue. Tissues with no expression of p185 include adrenal, blood vessel, brain parenchyma, cartilage, epididymis, heart, lymph node, spleen, striated muscle, testis, thymus, and thyroid.

Although the neu gene has been cloned, identification of the primary ligand for its protein product has been difficult. Though several endogenous p185 modulatory factors may exist, the effect of the primary ligand on p185 should be similar to those of EGF and PDGF on their receptors since these receptors are tyrosine kinases closely related to p185. Yarden, Y., (1988) *Annual Review of Biochemistry* 57:443; Yarden and Schlessinger,(1987) *Biochem.* 26:1443; Bishayee, et al., (1989) *J. Biol. Chem.* 264:11699.

It is an object of the invention to provide substances and methods for altering the cellular metabolism of mammals, particularly humans. It is also an object of the invention to provide substances for treating mammalian tumors, particularly human tumors. Current tumor treatments rely for the most part in the cytotoxic effects of drugs and radiological therapy. Although these treatments bring remission and cure to some patients, they unfortunately have serious side effects because they kill not only tumor cells but also some normal non-tumorous cells. There exists a great need for mammalian tumor treatments which affect primarily the tumor cells, but that have minimal interference with normal cells and cellular functions. It is a further object of the invention to provide methods for diagnosing tumors expressing p185 on the surfaces of the cells. Amplification of human neu gene and subsequent overexpression of the human neu gene product has been implicated in adenocarcinomas in several tissue types including breast, stomach, colorectal, ovary and pancreatic tissue. As a result, c-erbB-2 protein expression levels appear to be a useful prognostic indicator of breast, ovarian and lung cancers. These and other objects will become apparent to persons of ordinary skill in the art from a review of the present specification and the appended claims.

SUMMARY OF THE INVENTION

The present invention provides a purified proteinaceous substance which is selectively bindable with p185, the translation product of the neu gene and a method for purifying the proteinaceous substance. The proteinaceous substance of this invention has been named NAF which stands for "neu protein activating factor". When referenced herein, "NAF", "neu protein activating factor" and "proteinaceous substance" are equivalent and refer to the same compound. NAF increases the activity of the tyrosine kinase contained in the p185, but does not increase the activity of tyrosine kinase of the epidermal growth factor receptor. The proteinaceous substance induces p185 dimerization and internalization. In addition the proteinaceous substance of the invention affects the proliferation of neu-bearing cells. NAF is heat stable at 56° C. and 100 ° C. and is degradable by some proteases. The molecular weight of its smallest active/isolatable form is between about 7,000 and about 14,000 daltons. Forms of NAF having a molecular weight up to about 30,000 daltons exist with a second active range identified as occuring between about 14,000 and about 24,000 daltons. These larger forms may represent oligomeric forms of the smallest active/isolatable form.

In other embodiments, the invention also provides a method of treating a mammal to alter the metabolic state of the mammal which comprises administering the proteinaceous substance or a fragment thereof to the mammal in an amount effective to alter the metabolic state of the mammal. The invention additionally provides methods of treating mammalian tumors expressing p185. The proteinaceous substance and methods of the invention are useful for treating any type of cells which express p185 normally, as altered forms, or at altered levels.

The invention is more particularly pointed out in the appended claims and is described in its preferred embodiments in the following description.

DETAILED DESCRIPTION OF THE INVENTION

NAF may be purified from medium conditioned by T cells which have been transformed by human T cell lymphotrophic virus-1 (HTLV-1). A preferred cell line is ATL-2, an interleukin-2-independent HTLV(+) T cell line. The ATL- 2 cell line was deposited in the American Type Culture Collection, Rockville, Md. on Mar. 23, 1990 and has accession number CRL 10388. The endogenous source of this factor has proven to be elusive, perhaps because quantities of the factor are too low to be detected by the assays described herein.

In a preferred embodiment of the invention, ATL- 2 cells were washed two times with PBS, then cultured at $3 \times 10^5$/ml in serum-free RPMI 1640 medium (Whittaker M. A. Bioproducts, Inc., Walkersville, Md.)) for seventy-two hours. This culture supernatant is termed "conditioned medium" (C.M.) and was used for purification of NAF. Other media which will support ATL-2 cell growth may also be used for culture of the cells.

NAF may be prepared by ultrafiltration of conditioned medium using a membrane having a pore size of 1,000 daltons. Conditioned medium was fractioned and concentrated 100 fold by ultrafiltration using a YM-2 membrane (Amicon, Danvers, Mass.). Components in the conditioned medium having a molecular weight of less than 1,000 daltons pass through the membrane; whereas components of the conditioned medium having a molecular weight greater than 1,000 daltons remain in the concentrated conditioned medium. NAF is retained by the filter and is found in the fraction of conditioned medium containing components having a molecular weight of greater than 1,000 daltons.

NAF may be further purified by filtration of the conditioned medium followed by anion exchange chromatography, preferably using a diethylaminoethyl (DEAE) cellulose with high performance liquid chromatography (HPLC). Active fractions, determined using an in vitro immune complex kinase technique described in Example 7, or any other suitable assay that measures tyrosine kinase activity, are pooled, concentrated and subjected to reverse phase chromatography, preferably using a silica matrex column such as c18 (Waters, Inc., Milford, Mass.). Fractions determined to be active through an in vitro immune complex kinase as described in Example 7 or analogous technique have a relative specific activity of about 1000 times the original ATL-2 conditioned medium. NAF may be further purified by reverse phase chromatography using a second silica matrex column, preferably c18 (referred to herein as c18#2). Gel electrophoresis using a polyacrylamide gradient gel (Integrated Separation Systems, Hyde Park, Md. or PHorecast System by Amersham, Arlington Heights, Ill.) followed by silver staining of active fractions showed three unique bands at 10 kD, 20 kD and 26 kD which are characteristic of NAF.

The proteinaceous substance of the invention may be characterized by physical properties, its binding specificity for p185, its effects on the activity of neu protein, and by its effects on p185 bearing cells. NAF stimulates tyrosine kinase activity of p185neu, p185c-neu, and c-erb-B-2. The increase in tyrosine kinase activity may be tested by an immune complex kinase assay, as described in detail in Example 7 herein, or by any other suitable assay that measures tyrosine kinase activity.

The proteinaceous substance of the invention is stable to heat up to at least 100° C. This stability was determined by treatment of the C.M. for 30 minutes at 56° C. and 100° C. The proteinaceous substance exhibited normal activity after both treatments. In addition, treatment with chymotrypsin and bacterial protease showed that the proteinaceous substance of the present invention exhibits protease sensitivity.

NAF activation of p185 tyrosine kinase activity is dependent upon its specific binding to p185. Tests using antibodies which are specific for and block distinct epitopes on the extracellular domain of p185 indicated that the proteinaceous substance recognizes p185 at particular extracellular domains.

NAF has been found to cause its target protein, p185, to form dimers, or aggregates. This is a common reaction of receptor tyrosine kinases in response to their cognate ligands. Both homodimers and heterodimers are formed. Cross-linking studies, described herein, show that NAF causes a dose dependent increase in the formation of p185 homodimers in PN-NR6 cells. In cells which express both EGF and NAF, such as M1 cells, formation of a heterodimeric receptor structure (p185/EGFR) is dose dependent on treatment with either EGF or NAF.

Some tests show characteristics of NAF which are similar to other tyrosine kinase ligands such as EGF. These tests have indicated that NAF and EGF have similar mechanisms and functions, but are independent of each other. In response to exposure to their cognate ligands, receptor tyrosine kinases, such as p185, are down-regulated from the cell surface. NAF causes p-185 to down-regulate. Exposure to NAF caused a decrease in the surface expression of p185 by PN-NR 6 cells. Surface expression of EGFR on NE-19 cells was down modulated by the addition of EGF, but not NAF. This response appears to be temperature sensitive since incubation with NAF and EGF caused down-regulation of cells which were incubated at 37° C. but did not cause down-regulation of cells incubated at 4° C.

Finally, the effect of NAF on cells which express p185 was examined. NAF was shown to increase the soft agar growth capability of PN-NR6 cells which express p185. NAF had no effect on NE-19 cells which do not express p185. Neither NAF or EGF had growth promoting effects on parent NR-6 cells which express neither EGFR nor p185. Other growth factors have been tested and shown to be unrelated to this growth response. Growth factors such as TGF-α, TGF-β, and PDGF did not cause PN-NR6 or NR6 cells to proliferate.

Although the proteinaceous substance of the invention has initially been purified from a human cell line, proteinaceous substances from cells of other species that have the same or substantially the same binding affinity or are capable of binding with p185neu or p185cneu are also within the scope of the present invention. NAF has a molecular weight of about 7,000 to about 14,000. daltons based on gel filtration chromatography and ultrafiltration membrane analysis. NAF may also be present in forms having a molecular weight of about 14,000 to about 24,000 daltons. Gel electrophoresis using a polyacrylamide gradient gel (Integrated Separation Systems, Hyde Park, MD or PHorecast System by Amersham, Arlington Heights, Ill.) followed by silver staining indicates three unique bands at 10 kD, 20 kD and 26 kD in samples of NAF which have been purified through a second c18 purification step. The differing molecular weights of NAF indicate that it may exist in oligomeric, i.e. dimeric or trimeric forms. All the subunits of the proteinaceous substance, whether of the smaller or larger molecular weight forms, and multiples of subunits are within the scope of the invention. Fragments or portions of NAF, produced by any method including chemical synthesis, recombinant DNA techniques, degradation or modification of the purified proteinaceous substance or any combination of methods, that are capable of binding to p185neu are also within the scope of the invention. Further, fragments or portions of the proteinaceous substance that have been chemically modified, or produced in genetically engineered form as a fusion protein or containing amino acid residues not derived from the proteinaceous substance are also within the scope of the invention.

As noted, any combination of the subunits of the dimeric or trimeric forms of the proteinaceous substance of invention are also within the scope of the invention. The dimers or trimers may be comprised of two or three of the same subunits (i.e. homodimers or homotrimers), or two or three different subunits (i.e. heterodimers or heterotrimers). The subunits may be prepared by any suitable method including purification from natural sources, recombinant DNA techniques, chemical synthesis or any combination of methods. Suitable subunits also include fragments or portions of the proteinaceous substance. The subunits may also optionally be chemically modified, contain amino acids not derived from the proteinaceous substance of the invention, or contain amino acid sequences derived from synthesis as a fusion protein. The ability of portions or fragments of the proteinaceous substance of the invention, including any other form of the proteinaceous substance of the invention, to bind to p185 and affect cells expressing p185 on their surfaces may conveniently be determined using the assays described herein in the examples.

The proteinaceous substance of the invention is expected to be useful in treating mammalian diseases and conditions of cells expressing p185 on their surfaces. Without wishing to be bound by any particular theory or mode of action, it is presently believed that the proteinaceous substance of the invention will modulate the function of cells by binding to p185 on the surface of the cells which will then alter the enzymatic activity of the cell resulting in an alteration of the function of the cell.

For example, secretory epithelial cells express normal cellular p185 on their surfaces. Substances bindable with this receptor that stimulate cell growth or metabolism would be useful in situations where cell repopulation is needed such as after a burn or other type of cellular destruction or where it is desired to increase or restimulate metabolic products of the cell of their effects such as renewed hair growth from follicles of the skin.

The proteinaceous substance of the invention will be formulated and dosed according to the specific disorder to be treated, the condition of the individual patient, the site of delivery of the proteinaceous substance, the method of administration, and other factors known to practitioners. Thus, for the purposes herein, an effective amount of the proteinaceous substance is an amount that is effective to stimulate cellular metabolism, prevent, lessen the worsening of, alleviate or cure the condition for which the proteinaceous substance is administered.

The proteinaceous substance of the invention may be administered to the mammal in combination with a pharmaceutically acceptable carrier, such as sterile water, saline solution or other suffer, or in an emulsion. The proteinaceous substance of the invention may be administered to the cells of the mammal expressing p185 on their surfaces by any convenient route, such as oral, intravenous, subcutaneous, topical, and other modes of administration. The proteinaceous substance of the invention is administered to the mammalian patient at a concentration and for a length of time sufficient to modulate the metabolism of the cells. The particular concentration given will depend on such factors as the condition for which it is given, the age and weight of the recipient and the mode of administration.

The proteinaceous substance may also be combined with cytotoxic substances such as radiolabeled molecules and other compounds used for tumor treatment to increase the effect of the proteinaceous substance on cells expressing p185.

For the treatment of tumors overexpressing p185neu on the surfaces of the tumor cells or tumors expressing aberrant forms of p185, the proteinaceous substance of the invention, or active fragment or portion thereof, is administered to the tumor or the site of the tumor where it is expected to have an effect on the tumor.

The proteinaceous substance of the invention may also be used in the treatment of the tumors expressing both p185 and the epidermal growth factor receptor on the surfaces of the tumor cells. In this embodiment of the invention, the proteinaceous substance, or active fragment or portion thereof, and antibodies specific for the epidermal growth factor receptor are administered to a mammal having such a tumor in an amount effective to reduce tumor growth. Methods and reagents for treating such tumors may be found in copending application Ser. No. 07/386,820 filed Jul. 27, 1989 in the name of Mark I. Greene entitled "Methods of Treating Cancerous Cells With Anti-Receptor Antibodies", the disclosures of which are hereby specifically incorporated as if fully set forth herein. The proteinaceous substance of the invention is substituted for antibodies specific for p185 and is administered alone or in combination with antibodies specific for the epidermal growth factor receptor.

The proteinaceous substance of the invention may be used to diagnose tumors expressing p185 on the surface of the cells such as certain adenocarcinomas, breast, lung, and ovarian cancers, and to identify cells expressing p185. The proteinaceous substance of the invention is contacted with a tissue sample suspected of containing such tumor cells under conditions allowing binding of the proteinaceous substance to the tissue sample. Binding of the proteinaceous substance to cells in the tissue sample which indicates the presence in the tissue sample of tumor cells expressing p185 is then detected using conventional methods and commercially available reagents, such as antibodies specific for the proteinaceous substance that are labeled with an enzyme, fluorescent molecule, radiolabel, an electron dense compound such as ferritin, or a light scattering particle such as colloidal gold, or any combinations or permutations of the foregoing. Antibodies specific for the proteinaceous substance may be produced by standard techniques for producing polyclonal and monoclonal antibodies.

EXAMPLES

Abbreviations p185neu, the product of the rat neu oncogene; p185c-neu, the product of the rat neu proto-oncogene; c-erb-B-2, the human homologue of the rat neu gene product; p185 broadly refers to the oncogenic and proto-oncogenic neu gene product from rat, human, and other mammalian and vertebrate homologues of the neu gene product; HTLV-1, human T cell lymphotropic virus-1; FCS, fetal calf serum; EGFR, epidermal growth factor receptor.

The following examples are illustrative, but not limiting of the invention. Examples 1 and 2 describe the preparation and the physical characteristics of the proteinaceous substance of the present invention. Conditioned medium or partially purified conditioned medium was used in assays performed in Examples 4 through 14. A more purified form of the proteinaceous substance of the invention was used in Examples 15 through 21.

EXAMPLE 1

Preparation and Purification of Proteinaceous Substance

ATL-2 cell line is an IL-2-independent HTLV-1 (+) T cell line. Mycoplasm-free ATL-2 cells were maintained in RPMI 1640 medium containing 10% FCS as the culture medium (10% FCS-RPMI 1640) at 37° C. in a humidified atmosphere with 5% $CO_2$.

For purification of the proteinaceous substance, ATL-2 cells were washed twice in 1×PBS and cultured at $3\times10^5$/ml in serum-free RPMI 1640 medium/ 2 mM L-glutamine for seventy-two hours followed by pelleting of the cells. The culture supernatant so produced is termed "conditioned medium" (C.M.).

C.M. was concentrated 100 fold, from 1 liter to 10 ml, using a YM-2 Diaflo membrane (Amicon, Boston, Mass.) with a 1000d cutoff. For use in some assays, concentrated C.M. containing components greater than 1000 MW were rediluted to original volume with RPMI medium. Gel electrophoresis using a polyacrylamide gradient gel (Integrated Separation Systems, Hyde Park, MD or PHorecast System by Amersham, Arlington Heights, Ill.) followed by silver staining of some of this two column purified material from the one liter preparation revealed at least four to five bands of which the 10 kD and 20 kD bands were unique to this material. Passed C.M. containing components less than 1000 MW were used without dilution.

Concentrated C.M. was filter sterilized with a 0.45µ uniflo filter (Schleicher and Schuell, Keene, N.H.) and then further purified by application to a DEAE-SW anion exchange column (Waters, Inc. Milford, Mass.) which had been pre-equilibrated with 10 mM Tris-Cl, pH 8.1. Concentrated C.M. proteins representing one liter of original ATL-2 conditioned medium per HPLC run were absorbed to the column and then eluted with a linear gradient of 0 mM to 400 mM NaCl at a flow rate of 4 ml/min. Fractions were assayed using the in vitro immune complex kinase assay described in Example 7 with 10% of the appropriate DEAE fraction (1 column purified material) or 1% of the appropriate c18 fractions (two column purified material). The activity which increased the tyrosine kinase activity of p185c-neu in a dose-dependent manner using the in vitro immune complex kinase assay described in Example 7 was eluted as one dominant peak across 4 to 5 fractions (36–40) around 220 to 240 mM of NaCl. After HPLC-DEAE purification, the proteins in the active fractions were concentrated and pooled, concentrated and subjected to C18 (silica matrex) reverse phase chromatography (Waters, Inc., Milford, Mass.) (referred to as the c18#1 step or two column purified material). Elution was performed under a linear gradient of 2-propanol against 0.1% TFA. All the fractions were dialyzed against RPMI 1640 medium to remove the 2-propanol and assayed using the in vitro immune complex kinase assay, described in Example 7, and a 1% concentration of the appropriate fraction. The activity increasing the tyrosine kinase activity of p185c-neu was eluted in two peaks. One eluted in fraction 11–13, while a second, slightly less active peak of activity eluted in fractions 20–23. These two peaks correspond to around 5 to 7% of isopropanol and 11 to 14% isopropanol respectively. c18#1 generated fractions 11–13 were used in the characterization studies. Active fractions obtained from the second chromatographic step were pooled, and designated as the proteinaceous substance sample.

A twenty liter preparation employed the same purification strategy. The DEAE active fractions 35–41 were pooled and subjected to c18 chromatography as discussed above. c18#1 fractions 11–13 and 21–24 both had dose-dependent activity. The pool of fractions 11–13 was subjected to an additional c18 chromatographic step (referred to as c18#2 or three column purified material). Again fractions 11–13 and 21–24 had activity. The dose response of fraction 23 as determined by in vitro immune complex kinase assay as described in Example 7 may be obtained upon addition of 0.005% by volume fraction 23 and 0.05% by volume fraction 23. This represents the greatest purity achieved.

Molecular weight ranges were determined based on gel filtration chromatography and ultrafiltration membrane analysis. Near equal amounts of tyrosine kinase activity were retained and passed by a 10,000 molecular weight cut off filter. Almost all activity was passed by a 30,000 molecular weight cut off filter. Molecular weight ranges for active chromatographic fractions were determined by comparing fractions containing dose-dependent neu-activating activity to the elution profiles of a set of protein molecular weight standards (Sigma Chemical Co., St. Louis, Mo.) generated using the same running conditions. A low molecular weight region of activity was identified between 7,000 and 14,000 daltons. A second range of activity ranged from about 14,000 to about 24,000 daltons.

After gel electrophoresis using a polyacrylamide gradient gel (Integrated Separation Systems, Hyde Park, Md. or PHorecast System by Amersham, Arlington Heights, Ill.), silver staining of the three-column purified material (c18#2) was done with a commercially available silver staining kit (Biorad, Rockville Centre, N.Y.). Fraction 21,22,23, and 24 from c18#2 purification of the twenty liter preparation were run with markers. Fractions 22 and 23 showed the most potent dose response. Several bands unique to these fractions appear at molecular weights 10 kD, 20 kD and 26 kD.

EXAMPLE 2

Relative Specific Activity

As shown in Table 1, the relative specific activity of sample increases an estimated 1000 fold and as much as 3500 fold after purification.

Relative specific activity was determined by comparing the amount of activity in the original ATL-2 conditioned medium needed to generate a quantified dose-dependent increase in neu-kinase activity, with the amount of activity in single chromatographic-step purified material, and two chromatographic-step purified material needed to generate an equivalent response. Specific activity is the µg of total protein in an NAF-containing sample needed to increase the p185 band intensity, as quantified using a densitometer (LKB Ultrascan, Pharmacia LKB Biotechnology, Piscataway, N.J.), of the in vitro immune complex kinase assay as described in Example 7, 2.5 fold when compared to untreated sample. The in vitro immune complex kinase assay is disclosed in Example 7. 2.5 fold increases in p185 band intensity were obtained using 10% by volume original ATL-2 conditioned medium, 1% by volume pooled DEAE active fractions, and 0.01% c18#1 active fractions. The active fractions designated as c18#1 were used in biochemical and cellular characterization studies. The activity of the original ATL-2 conditioned medium was arbitrarily designated as 7000 units (7 units per ml original ATL-2 supernatant). Values for the total units of activity in the subsequent DEAE and c18 purification steps were based on the decreasing amount of material (1% by volume for DEAE sample and 0.01% by volume for the c18#1 material) needed to generate the same increase in band intensity as does the original ATL-2 supernatant when assayed at 10% by volume. Using these numbers it was estimated that there are 10 times more units and 1000 times more units per ml in the DEAE and c18#1 samples respectively when compared to the original ATL-2 conditioned medium. The increase in relative specific activity of approximately four fold for the DEAE generated material and approximately 250 fold for the c18#1 generated material are consistent with resolving capabilities of these two chromatographic techniques.

Along with the increase in relative specific activity, two other indicators of the increased purity may be noted. First, the activity of the pooled c18#1 separation was far greater than the original supernatant. Dimerization, down-modulation, and proliferation experiments were cleaner and more readily reproducible with c18#1 material, indicating an increased purity. The purified molecules were active even at reduced temperatures (<27° C.) in terms of dose response studies. The increased activity and function at lower temperatures also reflect increased proteinaceous substance purity.

TABLE 1

Specific Activity of Proteinaceous Substance at Different Stages of Purity

| | Concentration (µg/ml) | Volume (ml) | Total Protein (µg) | Activity (total unit) (unit/µg) | Relative Activity |
|---|---|---|---|---|---|
| Culture Supernatant | 7 | 1000 | 7000 | 7000 | 1 |
| DEAE Frac. 36–40) | 17 | 40 | 680 | 2800 | 4.11 |
| C18 No. 1 (Frac. 11–13) | 0.63 | 3 | 1.89 | 2100 | 1111 |

EXAMPLE 3

Maintenance and Characterization of Cell Lines

All cell lines were maintained in RPMI 1640 medium containing 10 % FCS and 2mM L-glutamine at 37° C. in a humidified atmosphere with 5 % $CO_2$. NR6 cells are a subclone of Swiss 3T3 cells which do not express detectable levels of EGFR, do not respond to EGF and do not express any p185. NR6 cells were co-transfected with PSV2-NEO and PSV2-neuN by the $Ca^{++}$ phosphate precipitation technique. The resulting cell line, called PN-NR6 (proto-oncogenic neu), expresses p185c-neu at high levels. NE-19 cells are NR6 cells transfected with a human EGFR gene and express EGFR at high levels. The M1 cell line was derived from NR6 cells and expresses EGFR and p185c-neu at high levels. These cell lines were described by Kokai et al., (1989) Cell 58:287. A431 cells (American Type Culture Collection) are a human spidermold carcinoma-derived cell line which express high levels of EGFR. SKBR111 cells are a human breast adenocarinoma-derived cell line which expresses both EGFR and c-erbB-2. B104 cells were derived from an ethyl-nitrosouria-induced rat neuroectodermal tumor. B104-1'-1' cells are NIH/w cells transfected with DNA originally isolated from the B104 cell line and later found to encode the neu oncogene. The NIH/w cell line is an NIH3T3 cell subclone which displays a low frequency of spontaneous tumor formation and which lacks EGFR.

EXAMPLE 4

Anchorage-Independent Growth Assay

Anchorage-independent growth capability was determined by assessing the colony-forming efficiency of cells suspended in soft agar. All experiments to determine colony-forming efficiency were conducted using 60 mm tissue culture dishes containing a 3 ml cell free feeder layer and a 1 ml top layer in which the cells were suspended. Feeder layers consisted of 0.24% agarose RPMI-1640 supplemented with 10% fetal calf serum, 2 mM L-glutamine. Overlayers contained 1×10⁴ cells in 0.18% agarose RPMI-1640 supplemented with 10% fetal calf serum, 2 mM L-glutamine. When sample containing proteinaceous substance was added to soft-agar cultures it was incorporated into the top layer only. Colonies larger than 0.5 mm in diameter were counted using a dissecting microscope at seven days. 4 random field (×100) were chosen from each 6 cm dish. Mean number was determined from these four fields to represent each 6 cm dish. Each experimental group represents the mean of triplicate dishes. In tables, a parenthesis shows the standard deviation of the triplicate samples.

EXAMPLE 5

Anchorage-Independent Growth Assay—Heat Treated Conditioned Medium

Conditioned medium (C.M.) were treated at 56° C. or 100° C. for thirty minutes. As shown in Table 2, both non-treated and heat-treated C.M. increased the colony formation of B104-1'-1'cells. This activity was stable even after heat-treatment.

TABLE 2

Anchorage Independence Assay B104-1'-1' Cells
Heat Treatment of Conditioned Medium

| | Concentration of Conditioned Medium | | |
|---|---|---|---|
| | 0% | 1.0% | 10% |
| No Treatment | | 10.00 (0.81) | 20.00 (5.88) |
| 56° C. treatment | | 7.50 (0.81) | 19.75 (6.13) |
| 100° C. treatment | | 14.00 (5.59) | 18.75 (2.98) |
| Control | 5.25 (2.62) | | |

EXAMPLE 6

Anchorage-Independent Growth Capability of Fractionated Conditioned Medium

The ability to increase the colony formation of B104- 1'-1' was contained in the C.M. concentrated by YM-2 membrane, which contains the components having a molecular weight of greater than 1000 dalton. Anchorage-independent growth capability of fractionated conditioned medium is shown in Table 3.

TABLE 3

Anchorage-Independent Growth Capability of
Fractionated Conditioned Medium

| | Concentration of C.M. | | |
|---|---|---|---|
| | 0% | 1.0% | 10% |
| No Treatment | | 17.50 (6.45) | 29.25 (7.13) |
| Concentrated | | 19.25 (5.61) | 56.25 (8.18) |
| Passed | | 15.25 (4.19) | 19.00 (5.29) |
| Control | 14.00 (4.19) | | |

EXAMPLE 7

Immune Complex Kinase Assay

This assay reflects the differences in the autophosphorylation activity of immunoprecipitated p185 driven by preincubation of PN-NR6 cell lysate with varying amounts of ATL-2 conditioned medium (C.M.) or proteinaceous substance and is referred to hereinafter as ned-activating activity. The cell lines are described in greater detail in Example 3.

Cell lines used in the immune complex kinase assay were obtained, prepared and cultured according to the methods disclosed in Kokai etal., Cell 58: 287–292, (Jul. 28, 1989) the disclosures of which are hereby incorporated by reference as if fully set forth herein, and U.S. application Ser. No. 386,820 filed Jul. 27, 1989 in the name of Mark I. Greene entitled "Methods of Treating Cancerous Cells With Anti-Receptor Antibodies", the disclosures of which are hereby incorporated by reference as if fully set forth herein.

Cell lines were all maintained in DMEM medium containing 5% FCS as the culture medium (5% FCS-DMEM) at 37° C. in a humidified atmosphere with 5% $CO_2$.

Dense cultures of cells in 150 mm dishes were washed twice with cold PBS, scraped into 10 ml of freeze-thaw buffer (150 mM NaCl, 1 mM $MgCl_2$, 20 mM Hepes, pH 7.2, 10% Glycerol, 1 mM EGTA, 1% Aprotinin), and centrifuged (600×6, 10 minutes). Cell pellets were resuspended in 1 ml Lysis buffer (50mM Hepes, PH 7.5, 150 mM NaCl, 3% Brij 35, 1 mM EDTA, 1.5 mM $MgCl_2$, 1% Aprotinin, 1 mM EGTA, 30 μM $Na_3VO_4$, 10% Glycerol) rotated for thirty minutes at 4° C. All chemicals were from Sigma Chemical Co., St. Louis, Mo., unless otherwise indicated. The insoluble materials were removed by centrifugation at 40,000×g for thirty minutes. The clear supernatant which was subsequently used is designated as cell lysate.

The cell lysates were incubated for fifteen minutes with 50 μl of 50% (volume/volume) Protein A-sepharose (Sigma Chemical Co., St. Louis, Mo.), and centrifuged for two minutes to preclear the lysates. 50 μl aliquots of precleared cell lysate were incubated on ice for fifteen minutes with conditioned medium, proteinaceous substance, or other factors as specified, in a final volume of 1 ml with lysis buffer. The sample was then incubated with 5 μg of 7.16.4. monoclonal antibody, which recognizes the extracellular domain of the p185neu and p185 c-neu, or other appropriate antibodies, for twenty minutes on ice, followed by a twenty minute incubation with 50 μl of 50% (vol/vol) protein A-sepharose with rotation at 4° C. Immune complexes were collected by centrifugation, washed four times with 500 μl of washing buffer (50mM Hepes, pH 7.5, 0.1%, Brij 35, 150 mM NaCl, 2 mM EDTA, 1% Aprontinin, 30 μM $Na_3VO_4$), then twice with reaction buffer (20 mM Hepes (pH7.4), 3 mM $MnCl_2$ and 0.1% Brij 35, 30 μM $Na_3VO_4$). Pellets were resuspended in 50 μl of reaction buffer and [Gamma- $^{32}P$] -ATP (Amersham, Arlington Heights, Ill.) was added giving a final concentration of 0.2 μM. The samples were incubated at 27° C. for twenty minutes or at 4° C. for 25 minutes with purer samples. The reactions were terminated by addition of 3×SDS sample buffer containing 2 mM ATP and 2 mM EDTA and then incubating them at 100° C. for five minutes. The samples were then subjected to SDS-PAGE analysis on 10% acrylamide gels. Gels were stained, dried, and exposed to Kodak XAR or XRP film with intensifying screens.

EXAMPLE 8

Effect of C.M. on Kinase Activity of PN-NR6 and M1 Cells

Lysates of PN-NR6 and M1 cells were treated as described in Example 7 and received the following: No addition (control); 0.1% of C.M.; 1.0% of C.M.; or 10% of C.M. The addition of conditioned medium increased tyrosine kinase activity of p185c-neu from PN-NR6 and M1 cells at all concentrations of conditioned medium. There was a two to four fold increase in p185 band intensity in lanes representing 10% conditioned medium treatment as compared to lanes with no conditioned medium treatment.

EXAMPLE 9

Effect of Conditioned Medium On Tyrosine Kinase Activity Of Epidermal Growth Factor Receptor Tyrosine kinase activity was determined using the immune complex kinase assay described in Example 7. Lysates of A431 cells were treated as described and received the following: No addition (control), 0.1 ng/ml 1.0 of EGF; 1.0 ng/ml of EGF; 10 ng/ml of EGF; 0.1% of C.M.; 1.0% of C.M.; or 10% of C.M. The addition of EGF increased the tyrosine kinase activity of EGFR from A431 cells. The addition of conditioned medium did not increase the tyrosine kinase activity of EGFR from A431 cells. Tyrosine kinase activity of epidermal growth factor receptor (EGFR) is increased by addition of EGF but not conditioned medium. This indicates the receptor specificity of the factor.

EXAMPLE 10

Effect Of Conditioned Medium On Phosphorylation Of Histone By Kinase Of p185c-neu Tyrosine kinase activity was determined using the immune complex kinase assay described in Example 7. Lysates of PN-NR6 cells were treated as described and received the following: No addition; 1.0% of C.M.; or 10% of C.M. 2μl of histone (2 mg/ml) was added with $^{32}$P-r-ATP as substrates of tyrosine kinase of p185c-neu. The phosphorylation of histones by tyrosine kinase of p185c-neu was increased two to six fold by addition of conditioned medium.

EXAMPLE 11

Effect Of Heat Treatment On Tyrosine Kinase Activity Of p185c-neu

Tyrosine kinase activity was determined using the immune complex kinase assay described in Example 7. C.M. were treated at 56° C. or 100° C. for thirty minutes. Lysates of PN-NR6 cells were then treated as described and received the following: No addition; 1.0% of heat-treated or non-treated C.M.; 10% of heat-treated or non-treated C.M. The activity contained in the C.M. was stable after heat treatment at either 56° C. or 100° C. for thirty minutes. Thus the p185c-neu tyrosine kinase activating activity in the C.M. is not affected by heat treatment.

EXAMPLE 12

Tyrosine Kinase Activity Of Fractionated Conditioned Medium

Conditioned medium was concentrated as described in Example 1. Concentrated C.M. containing components greater than 1000 MW were rediluted to original volume by distilled water and used in assays. Passed C.M. containing components less than 1000 MW were used without dilution. Tyrosine kinase activity was determined using the immune complex kinase assay described in Example 7. Lysates of PN-NR6 cells were treated as described and received the following: No addition; 1.0% of C.M.; 10% of C.M.; non-treated C.M.; concentrated C.M.; passed C.M. Increased tyrosine kinase of p185c-neu was contained in concentrated C.M. with a molecular weight greater than 1000. Near equal amounts of activity were retained and passed by a 10,000 molecular weight cut off filter. Almost all activity was passed by a 30,000 molecular weight cut off filter.

EXAMPLE 13

Effect Of Protease On Tyrosine Kinase Activity Of Conditioned Medium

Tyrosine kinase activity was determined using the immune complex kinase assay described in Example 7. A first portion of C.M. was treated with 100μg alpha-chymotrypsin (Sigma, St Louis, Mo.) for two hours at 37° C. The reaction was stopped by adding 2-fold molar excess of chymotrypsin-inhibitor (Sigma, St. Louis, Mo.) A second portion of C.M. was treated with 100 μg bacterial protease (Sigma, St. Louis, Mo.) for two hours at 37° C. The reaction was stopped by heat-inactivating the protease by boiling for five minutes. Lysates of PN-NR6 cells were treated as described and received the following: A) No addition; B) C.M. treated by chymotrypsin, no inhibitor added; C) C.M. treated by chymotrypsin-inhibitor only; D) C.M. treated by chymotrypsin, then treated by inhibitor; E) C.M. treated by chymotrypsin which was previously inactivated by chymotrypsin inhibitor; F) C.M. treated by bacterial protease, then heat-inactivated; G) C.M. treated by bacterial protease which was pre-inactivated by heat treatment; and H) non-treated C.M.

After SDS/PAGE, the band intensity of protease treated p185c-neu samples was less than those samples that were not treated with protease. Band intensity of protease treated samples was also less intense than bands of samples treated with protease wholly or partly inactivated with protease inhibitor or heat treatment. These data indicate that the p185c-neu-specific activity in the C.M. is sensitive to digestion by chymotrypsin and bacterial protease.

EXAMPLE 14

Effect of Conditioned Medium On Binding Activity Of Antibody To p185-neu

Tyrosine kinase activity was determined using the immune complex kinase assay described in Example 7. C.M. was added before immunoprecipitation by 7.16.4 monoclonal antibody. Monoclonal antibody 7.16.4 recognizes the extracellular domain of p185neu and p185c-neu. p185c-neu (from PN-NR6 cells) was immunoprecipitated by 7.16.4 monoclonal antibody and immune complexes were washed by washing buffer once and then immune complexes were incubated with C.M. for fifteen minutes at 4° C. After these steps, the immune complex kinase assay, set forth in Example 7, was performed as described herein. Lysates of PN-NR6 were treated as described and received the following: No addition; 1.0% of C.M.; and 10% of C.M. Tyrosine kinase activity of C.M. was blocked by pretreatment with 7.16.4 monoclonal antibody. These data show that a component in the conditioned medium binds with p185c-neu.

EXAMPLE 15

Effect of ATL-2 secreted growth modulating substances on the kinase activity of p185c-neu Growth modulating substances such as ADF (IL-2 receptor inducing factor), TGF-α (transforming growth factor α), TGF-β (transforming growth factor β), PDGF (platelet derived growth factor), IL-1 (interleukin 1) and IL-6 (interleukin 6) which are secreted from the ATL-2 cell line were tested using the in vitro immune complex kinase assay, as set forth in Example 7. None of these factors-affected the kinase activity of p185c-neu. Representative of results obtained was treatment of PN-NR6 lysate with 10 or 100 units of IL-1 or 25 or 250 units of IL-6 which resulted in no increase in kinase activity.

EXAMPLE 16

Effect of NAF and EGF on the phosphotyrosine content of p185 and EGFR expressed in identical fibroblast cell background Western blot analysis as described in Wada et al., (1990) Cell 61:1339, was employed to demonstrate that the quantity of phosphotyrosine in p185 was specifically increased by the addition of NAF. Intact PN-NR6 (p185+/EGRF−) and NE-19 (EGRF+/p185−) cells (2×10$^6$) in 10 cm culture dishes were incubated for 8 minutes at 37° C. with 0, 0.1 or 1.0% by volume NAF or0, 10 or 100 ng/ml EGF. The cells were washed three times with cold phosphate buffered saline containing 400 EDTA, 10 mM sodium pyrophosphate, 10 mM sodium fluoride and 400 μM sodium orthovanadate and were lysed in PI/RIPA buffer (1% Triton X-100, 1% Deoxycholate, 0.1% SDS, 0.15 M NaCl , 0.01 M sodium pyrophosphate pH 7.4,1% trasylol, 1 μM PMSF, 2 mM EBTA, 10 mM sodium fluoride, 10 mM sodium pyrophosphate, 400 μM sodium orthovanadate, 10 mM iodo-acetamide, and 1 mM ATP) for 30 minutes. Pre-cleared supernatants were subjected to immunoprecipitation with monoclonal antibody 7.16.4 (which reacts specifically with rat p185) or anti-EGFR carboxy terminal antibodies (provided by Dr. Stuart Decker, Rockefeller University, New York, N.Y.) respectively. Immunoprecipitates were washed 2 times with washing buffer (0.1% Triton X-100, 0.4 mM EDTA, 10 μM sodium fluoride, 10mM Sodium pyrophosphate, 400 μM Sodium orthovanadate, 0.01 M sodium phosphate, pH 7.4). Washed immunoprecipitates were boiled in SDS-sample buffer (pH6.8) (3% SDS, 10% glycerol, 5% 2ME, 0.4% bromophenol blue) and analyzed on 10% SDS-PAGE gels. Proteins were transferred to nitrocellulose and detected by anti-phosphotyrosine antibody PY-20 MAb (ICN Biomedicals, Inc., Costa Mesa, Calif.) as described in Wada et al., (1990) Cell 61:1339.

The amount of phosphotyrosine in p185c-neu from PN-NR6 cells (p185+/EGFR−) was increased by addition of 0.1% or 1.0% " NAF in a dose-dependent manner while addition of 10 and 100 ng/ml EGF had no effect under the same conditions. The amount of phosphotyrosine detectable in EGFR from NE-19 cells (EGFR+/p185−) was increased by addition of 10 or 100 ng/ml EGF but was not increased by addition of 0.1% or 1.0% NAF. NAF affected the tyrosine kinase activity of p185c-neu expressed in the NR6 cell background (PN-NR6 cells) yet had no effect on EGFR in the identical NR6 cell background (NE-19 cells) again indicating that the observed effects are not mediated by EGF and its receptor. Controls with no addition of NAF or EGF produced no response in either cell line.

EXAMPLE 17

NAF Interacts with the Extracellular Domain of the neu Protein p185

Monoclonal antibodies specific for distinct epitopes on the extracellular domain of p185 were examined for their ability to block the NAF-mediated increase of p185 kinase activity using the immune complex kinase assay as described in Example 7. PN-NR6 cells were pre-incubated with 1 μg/ml antibody or no antibody (control) at 4° C. for 30 minutes, and then washed twice with cold PBS. Cells were then exposed to 1% (by volume) NAF or no NAF (control) and incubated at 37° C. for 10 minutes. Cells were lysed, p185 was immunoprecipitated with 7.16.4, an anti-p185 antibody, and the immune complex kinase assay was performed as described in Example 7.

Pre-incubation of PN-NR6 cells (p185+/EGFR−) with purified p185 extracellular domain specific monoclonal antibody 7.16.4 (Drebin et al., (1984) Nature 312:545; Drebin et al., (1985) Cell 41:695) blocked the NAF-induced activation of p185, while an irrelevant, isotype matched monoclonal antibody 9BG5, an IgG2a monoclonal antibody reactive with the reovirus type 3 hemaglutanin (Drebin et al., (1988) Oncogene 2:273) did not block the NAF-induced activation of p185. Monoclonal antibody 7.9.5 recognizes a distinct extracellular domain of p185 (Drebin et al., (1988) Oncogene 2:273) and only partially blocked the NAF-induced activation of p185. Similarly, pre-incubation of cells with suramin, which has been shown to block EGF and PDGF from binding to their receptors (Yarden and Weinberg, (1989) Proc. Natl. Acad. Sci. U.S.A. 86:3179 and L. T. Williams, et al., (1984) J. Biol. Chem. 259:5287) blocked the NAF-induced activation of p185. In addition, western blot analysis with anti-phosphotyrosine monoclonal antibodies was performed using a mutant p185, termed p185-D4 which contains a 523 based pair deletion corresponding to amino acids 475 through 648 (in frame) of the second cysteine rich domain of the extracellular region of p185c-neu. NAF did not increase the kinase activity of this p185 mutant (transfected into NR6 cells) that lacks this portion of the extracellular putative ligand-binding domain of p185c-neu. Collectively these results indicate that NAF interacts with discrete parts of the neu protein extracellular domain.

EXAMPLE 18

Effect of NAF on p185 Dimerization

Receptor tyrosine kinases are induced by their cognate ligands to form receptor aggregates. Homodimeric and heterodimeric species of p185-neu have previously been described. The point mutation (from adenine to glutamic acid at residue 664) in the transmembrane region of p185-neu is able to facilitate homodimer formation (Weiner, et al., (1989) Nature pb 338:230).

Cross-linking studies were performed to determine the effect NAF on p185 dimerization. Chemical cross linking was done as described by Wada et al., (1990) Cell 61:1339. 3×10$^6$ cells in 10 cm culture dishes were plated and incubated with 5% FCS overnight. Medium was then replaced by ITS-DMEM and cultured overnight. Cells were incubated with or without ITS-DMEM supplemented with or without the indicated amount of NAF or EGF at 37° C. for 8 minutes and them washed twice with cold PBS. Five ml of PBS containing 4 mM BS$_3$ (Pierce, Rockford, Ill.) was added and cells were incubated at 22° C. for 30 minutes. The cross linking reaction was quenched by addition of quenching buffer. Cells were then solubilized and their lysates were subjected to immunoprecipitation with 7.16.4 antibody. Proteins were then separated on 4%–7.5% gradient SDS-PAGE minigels and transferred to nitrocellulose. Monomeric and dimeric forms of p185c-neu were detected with anti-phosphotyrosine MAb PY-20 (ICN Biomedicals, Inc., Costa Mesa, Calif.) and DBW2 (anti-p185 intracellular domain) antibodies. Antibodies were detected with $^{125}$I-Protein A (New England Nuclear, Boston, Mass.).

Cross-linking studies revealed that the amount of p185c-neu homodimers in PN-NR6 cells (p185+/EGFR−) was increased in a dose dependent manner with exposure to 0.1% or 1.0% NAF. A control with no addition of NAF produced no response. The amount of phosphotyrosine in the p185c-neu homodimers also increased in a dose-dependent manner with addition of 0.1% or 1.0% NAF. Heterodimeric species of p185c-neu have recently been described Kokai et al., (1989) Cell 58:287; Wada et al., (1990) Cell 61:1339. In M1 cells, which express high levels of both p185c-neu and EGFR, Kokai, et al., (1989) Cell 58:287, p185c-neu/EGFR heterodimers exist and EGF treatment of M1 cells also increased the amount of detectable p185c-neu/EGFR heterodimers in a dose-dependent manner.

EXAMPLE 19

Effect of NAF and EGF on p185 and EGFR Internalization

In response to exposure to their cognate ligands, receptor tyrosine kinases are down regulated from the cell surface. The ability of NAF to down modulate p185c-neu from the surface of PN-NR6 cells was examined by quantitative immunological assessment of the amount of cell surface p185 on PN-NR6 cells after treatment with NAF.

p185c-neu down modulation assay was performed as described by Yarden and Weinberg,(1989) Proc. Natl. Acad. Sci. U.S.A. 86:3179. Cells were cultured overnight in DMEM containing ITS and incubated with NAF or EGF for the indicated time period. 1×10$^5$ PN-NR6 or NE19 cells in 24 well dishes (Costar, Cambridge, Mass.) were seeded and incubated overnight in DMEM medium containing 5% fetal calf serum (FCS). Those cells were washed with DMEM and incubated 1 hour with DMEM and then incubated with binding buffer [DMEM supplemented with 20mM Hepes (pH 7.2) and 0.1% bovine serum albumin] with or without 1% NAF(by volume) or 50 ng/ml EGF. After incubation at 37° C., the monolayer was washed with DMEM and incubated at 4° C. with 2 μg/ml of the 7.16.4 or anti-EGFR antibody. This monoclonal antibody recognizes the extracellular domain of human EGF receptor and was provided by Dr. M. Herlyn of the Wistar Institute, Philadelphia, Pa. After a 2 hour incubation, cell-bound antibody was determined by a 45-minute incubation with $^{125}$I-labeled protein A.

Surface expression of p185c-neu on PN-NR6 cells was decreased by 30% at 30 minutes and by 40% at 90 minutes after the addition of NAF while EGF has no effect on the internalization of p185c-neu in these same cells. Surface EGFR on NE-19 cells was down-modulated by the addition EGF, but was not down-modulated by proteinaceous substance. When the cells were incubated with NAF or EGF at 4° C. rather than 37° C., neither p185c-neu nor EGFR could be down modulated on either cell type.

EXAMPLE 20

Effect of NAF and Other Factors on Cell Growth measured by [$^3$H]-Thymidine Incorporation The effect of NAF on the growth of cells was assessed using tritiated thymidine incorporation. Subconfluent cells were trypsinized and 1×10$^4$ cells were suspended in DMEM medium containing 10% FCS and placed in 96-well plate. Following cell attachment overnight, the medium was replaced with DMEM medium suplemented with ITS (a defined culture medium having insulin, transferrin and selenium as three of its most common components (Collaborative Research, Bedford, Mass.). Incubation was continued in this serum-free medium for an additional 48 hours. Thereafter, cells were exposed to NAF, EGF (epidermal growth factor), TGF-α (transforming growth factor e), TGF-β (transforming growth factor β), or PDGF (platelet derived growth factor) factors for 16 hours. Cells received a 6 hour pulse of [$^3$H] thymidine (0.5 uCi/ml) prior to harvest.

NAF increased the relative levels of DNA synthesis in cultures of PN-NR6 cells (p185+/EGFR). 1.0% NAF increased the DNA synthesis three fold. NAF did not affect the levels of DNA synthesis in cultures of NE-19 cells (p185−/EGFR+). DNA synthesis in cultures of NE-19 cells was increased two fold by the increase of EGF from 10 ng/ml to 100 ng/ml. Neither EGF, TGF-α (10 ng/ml or 100 ng/ml), TGF-β (10ng/ml), or PDGF (10 ng/ml) factors significantly affected the DNA synthesis cultures of PN-NR6 cells.

EXAMPLE 21

Anchorage-Independent Growth Assays—Capability of Factors

Anchorage-independent growth assays were performed as described in Example 4 to determine the growth capabilities of NAF, EGF, TGF-α, TGF-β, and PDGF on PN-NR6, NE-19 and NR- 6 cell lines. Results are set forth in Table 4.

PN-NR6 cells do not oridinarily form colonies in soft agar while NIH/3T3 transfectants which overexpress EGFR form colonies in soft agar only upon addition of EGF (DiFiore et al. (1987) Cell 51:1063). NAF also increased the soft agar growth capability of PN-NR6 cells (p185+/EGFR−), but had no effect on NE-19 cells (EGFR+/p185−). Conversely, EGF increased the soft-agar growth capability of NE-19 cells, but had no effect on the neu-bearing PN-NR6 cells. The parent NR-6 cells (p185−/EGFR−) were not affected by EGF or by NAF. Thus, the growth promoting effects of the proteinaceous substance were seen only in cells that express p185c-neu. Furthermore it is unlikely that other factors are responsible for these results since TGF-α, TGF-β, and PDGF did not cause PN-NR6 or NR6 cells to proliferate or form colonies in soft agar.

TABLE 4

| Effect of Growth Factors on Cell Growth | | | | |
| --- | --- | --- | --- | --- |
| Factor | Concentration | PN-NR-6 | NE-19 | NR-6 |
| — | — | 0 | 0 | 0 |
| NAF | 0.1 | 6 | 0 | 0 |
| (%) | 1.0 | 25 | 0 | 0 |
| EGF | 10 | 0 | 22 | 0 |
| (ng/ml) | 100 | 0 | 30 | 0 |
| TGF-α | 10 | 0 | n.d* | n.d |
| (ng/ml) | 100 | 0 | n.d | n.d |
| TGF-β | 1 | 0 | n.d | n.d |
| (ng/ml) | 10 | 0 | n.d | n.d |
| PDGF | 1 | 0 | n.d | n.d |
| (ng/ml) | 10 | 0 | n.d | n.d |

*n.d = not determined

We claim:
1. A purified proteinaceous substance which is bindable with p185, wherein said proteinaceous substance:
   increases the activity of the tyrosine kinase contained in p185 but does not increase the activity of tyrosine kinase of epidermal growth factor receptor;

induces p185 dimerization;

induces p185 internalization;

affects the growth of cells which express p185 in a dose dependent manner;

is heat stable from about 56° C. to about 100° C.;

is degradable by protease; and has a molecular weight of from about 7,000 to about 14,000 daltons or a fragment thereof having binding affinity for p185.

2. A dimer of the proteinaceous substance of claim 1.

3. A trimer of the proteinaceous substance of claim 1.

4. A method of screening for a mammalian tumor that has p185 on the surfaces of the tumor cells comprising the steps of:

contacting suspected tumor cells with the proteinaceous substance of claim 1 under binding conditions; and detecting bound proteinaceous substance, wherein the presence said bound proteinaceous substance indicates the presence of p185.

5. The method of claim 4 wherein said proteinaceous substance a) is a fragment of a proteinaceous substance that:
   i) increases the activity of the tyrosine kinase contained in p185 but does not increase the activity of tyrosine kinase of epidermal growth factor receptor;
   ii) is heat stable from about 56 to about 100° C.;
   iii) is degradable by protease; and
   iv) has a molecular weight of from about 7,000 to about 14,000 daltons; and
b) has binding affinity for p185.

6. The purified proteinaceous substance of claim 1 wherein said proteinaceous substance a) is a fragment of a proteinaceous substance that:
   i) increases the activity of the tyrosine kinase contained in p185 but does not increase the activity of tyrosine kinase of epidermal growth factor receptor;
   ii) is heat stable from about 56° to about 100° C.;
   iii) is degradable by protease; and
   iv) has a molecular weight of from about 7,000 to about 14,000 daltons; and
b) has binding affinity for p185.

7. A purified proteinaceous substance which is bindable with p185, wherein said proteinaceous substance:

increases the activity of the tyrosine kinase contained in p185 but does not increase the activity of tyrosine kinase of epidermal growth factor receptor;

is heat stable from about 56° to about 100° C.;

is degradable by protease; and has a molecular weight of from about 7,000 to about 14,000 daltons.

8. A dimer of the proteinaceous substance of claim 7.

9. A trimer of the proteinaceous substance of claim 7.

10. A method of screening for a mammalian tumor that has p185 on the surfaces of the tumor cells comprising the steps of:

contacting suspected tumor cells with the proteinaceous substance of claim 7 under binding conditions; and detecting bound proteinaceous substance, wherein the presence said bound proteinaceous substance indicates the presence of p185.

11. An isolated protein fraction from ATL-2 cells comprising a purified proteinaceous substance which is bindable with p185, wherein said proteinaceous substance:

increases the activity of the tyrosine kinase contained in p185 but does not increase the activity of tyrosine kinase of epidermal growth factor receptor;

is heat stable from about 56° to about 100° C.;

is degradable by protease; and has a molecular weight of from about 7,000 to about 14,000 daltons.

12. A dimer of the proteinaceous substance of claim 11.

13. A trimer of the proteinaceous substance of claim 11.

14. A method of screening for a mammalian tumor that has p185 on the surfaces of the tumor cells comprising the steps of:

contacting suspected tumor cells with the isolated protein fraction of claim 11 under binding conditions; and detecting bound proteinaceous substance, wherein the presence said bound proteinaceous substance indicates the presence of p185.

* * * * *

UNITED STATES PATENT AND TRADEMARK OFFICE
CERTIFICATE OF CORRECTION

PATENT NO. : 5,464,751
DATED : November 7, 1995
INVENTOR(S) : Greene et al.

It is certified that error appears in the above-indentified patent and that said Letters Patent is hereby corrected as shown below:

Col. 5, line 38, after "14,000" delete the period "."

Col. 12, line 1, change "ned" to --neu--.

Col. 15, line 20, after "or" first occurrence, there should be a space before the --O--.

Col. 16, line 47, after "Nature" the name of the publication delete "pb338" and insert --339--.

Signed and Sealed this

Thirteenth Day of February, 1996

Attest:

BRUCE LEHMAN

Attesting Officer      Commissioner of Patents and Trademarks